(12) United States Patent
Lin et al.

(10) Patent No.: US 9,056,067 B2
(45) Date of Patent: *Jun. 16, 2015

(54) PHARMACEUTICAL COMPOSITION FOR ENHANCING IMMUNITY, AND EXTRACT OF PORIA

(71) Applicant: Sinphar Pharmaceutical Co., Ltd., I Lan (TW)

(72) Inventors: Hang-Chin Lin, Taipei (TW); Jerming Tseng, Taipei (TW); Hsiou-Yu Ding, Tainan (TW); Wen-Liang Chang, Taipei (TW); Chien-Lian Chao, Taoyuan (TW); Hsin-Wen Huang, Taipei (TW)

(73) Assignee: Sinphar Pharmaceutical Co., Ltd., I Lan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,989

(22) Filed: Nov. 1, 2013

(65) Prior Publication Data

US 2014/0065174 A1  Mar. 6, 2014

Related U.S. Application Data

(62) Division of application No. 12/838,545, filed on Jul. 19, 2010, now abandoned, which is a division of application No. 10/717,559, filed on Nov. 21, 2003, now abandoned.

(30) Foreign Application Priority Data

May 16, 2003 (TW) .............................. 92113393 A

(51) Int. Cl.
*A61K 36/076* (2006.01)
*A61K 39/00* (2006.01)
*A61K 31/56* (2006.01)
*A61K 31/575* (2006.01)

(52) U.S. Cl.
CPC .............. *A61K 39/00* (2013.01); *A61K 36/076* (2013.01); *A61K 31/56* (2013.01); *A61K 31/575* (2013.01)

(58) Field of Classification Search
None
See application file for complete search history.

(56) References Cited

U.S. PATENT DOCUMENTS 8,658,629 B2 * 2/2014 Lin ................................ 514/180
2009/0318399 A1 * 12/2009 Lin et al. ....................... 514/180

FOREIGN PATENT DOCUMENTS

JP  08-119864 A  * 5/1996
JP  2005-089328 A  * 4/2005

OTHER PUBLICATIONS

Cuellar (Chem. Pharm. Bull. (1997), vol. 45, No. 3, pp. 492-494).*

* cited by examiner

*Primary Examiner* — Susan Hoffman
(74) *Attorney, Agent, or Firm* — Cesari and McKenna, LLP

(57) ABSTRACT

A pharmaceutical composition is used to enhance immunity of the human body. The composition contains potent components of lanostane compounds. A method is devised to obtain an extract from metabolite, sclerotium, or fermentation product of *Poria cocas* (Schw) Wolf. The extract contains 5-60% of the lanostane compounds by weight of the extract. The extract is devoid of secolanostane capable of inhibiting immunity development.

16 Claims, 2 Drawing Sheets

PHARMACEUTICAL COMPOSITION FOR ENHANCING IMMUNITY, AND EXTRACT OF PORIA

RELATED APPLICATIONS

This is a divisional application of U.S. application Ser. No. 12/838,545, filed Jul. 19, 2010, now abandoned, which is a divisional application of U.S. application Ser. No. 10/717,559, now abandoned, filed Nov. 21, 2003; which claims priority to Taiwan, Republic of China Application No. 92113393, filed May 16, 2003. All of the above applications are incorporated into the current divisional application by reference.

FIELD OF THE INVENTION

The present invention relates to a pharmaceutical composition containing lanostane as a potent component thereof for enhancing immunity. The present invention further relates to an extract of *Poria cocos* (Schw) Wolf for the purpose of immunity enhancement.

BACKGROUND OF THE INVENTION

The *Poria* extract has tonic effect, as well as a smoothing effect on stomach disorder. According to the Chinese medicine, the *Poria* extract is classified as a tranquilizer and a uretic agent. In addition, the *Poria* extract is used as one of essential ingredients of the Chinese medicine prescription for vital activity. On the basis of researches and experiments, which have been conducted in recent years on the pharmacological effect of the *Poria* extract, it has been concluded that the *Poria* extract has a favorable effect on tumor prevention, and that the *Poria* extract is beneficial to immunity enhancement and gastrointestinal system of a person suffering from a chronic disease.

As exemplification, the Japan Patent Publication Numbers 55-111791 and 57-38794 disclose an extract which is obtained from the cultivated mycelia of *Poria cocos* (Schw) Wolf and is effective in tumor prevention. The Japan Patent Publication No. 55-111422 discloses an extract which is directly obtained from *Poria cocos* (Schw) Wolf for use in tumor prevention. The Japan Patent Publication No. 8-119864 discloses an extract which is obtained by extracting *Poria cocos* (Schw) Wolf with methanol. By separation, triterpene compounds such as lanostanes and secolanostanes are obtained from the extract and are used as anti-emetic agents. The Japan Patent Publication No. 9-025232 discloses triterpene compounds, which is obtained by extracting *Poria cocos* (Schw) Wolf with methanol. The compounds are useful as a tumor promotion-inhibiting agent. The Japan Patent Publication No. 9-176184 discloses an extract of *Poria cocos* (Schw) Wolf, which is then refined to produce triterpene compounds for use as an agent for inhibiting inflammation and tumor promotion.

The China Patent Publication No. 1008183 discloses a method of making a *Poria* extract containing triterpene compounds. The method involves extracting the *Poria* powder with an acidic alcohol, neutralizing the extract with a basic solution, concentrating the neutralized solution, adjusting the pH thereof to about 10 and filtering the solution, acidifying the filtrate to form a precipitate, washing the precipitate after filtration, and drying the washed precipitate. The *Poria* extract so obtained is found to have a tumor-preventive effect and an immunity activation effect.

SUMMARY OF THE INVENTION

The primary objective of the present invention is to provide a method of prepare a potent component having an improved biological activity from *Poria cocos* (Schw) Wolf, and a *Poria* extract containing the potent component.

It is another objective of the present invention to provide a method of using *Poria cocos* (Schw) Wolf to prepare a potent component capable of enhancing immunity of mammal, and a *Poria* extract containing the Potent component.

It is still another objective of the present invention to provide a new use of lanostane. One aspect of this use is a pharmaceutical composition for enhancing immunity of mammal. A pharmaceutical composition embodied according to the present invention contains one or more lanostane compounds. The pharmaceutical composition is used to adjust or enhance immunity and can be dispensed by a dermal, oral, or hypodermic administration, and may be in a slow-release dosage form.

The present invention makes use of the immunity experiments to verify the pharmacological properties of the potent component of the *Poria* extract. The potent component is a low polarity portion (PCM), which contains major compounds of K1, K2, K3, K4, and trace of K4a, K4b, K5, K6a, K6b, which are all lanostane compounds. The compounds of K1, K2, K3, and K4 have an immunity enhancement effect.

The method of the present invention makes use of the conventional extraction process, by means of which a crude extract is obtained. A chromatographic separation is used to separate constituents of the crude extract, which include a lanostane fraction and a secolanostane fraction. The lanostane fraction is relatively smaller in polarity than the secolanostane fraction. The lanostane fraction is obtained by using an eluent made of dichloromethane:methanol=96:4, whereas the secolanostane fraction is obtained by using an eluent made of dichloromethane:methanol=90:10 or 0:100. The position of the lanostane fraction is identified by the thin layer chromatography, which has a chromatographic value (Rf) being ≥0.1 when a developing solution of dichloromethane:methanol (96:4) is used. The chromatographic value of the secolanostane fraction is smaller than 0.1. By a silica gel column chromatography, the lanostane fraction is separated into several lanostane compounds with an eluent made of dichloromethane:methanol alcohol=97:3 to 95:5.

According to the method of the present invention, 2.6 grams of PCM are obtained from one kilogram of *Poria cocos* (Schw) Wolf. According to the method of the China Patent Publication No. 1008183, three grams of a crude extract are obtained from one kilogram of *Poria cocos* (Schw) Wolf. When this crude extract is purified by the method of the present invention, only one gram of PCM is obtained.

The features of the present invention will be more readily understood upon a thoughtful deliberation of the following detailed description of the nonrestrictive embodiments of the present invention with reference to the accompanying drawings.

DETAILED DESCRIPTION OF THE INVENTION

Figure 1:
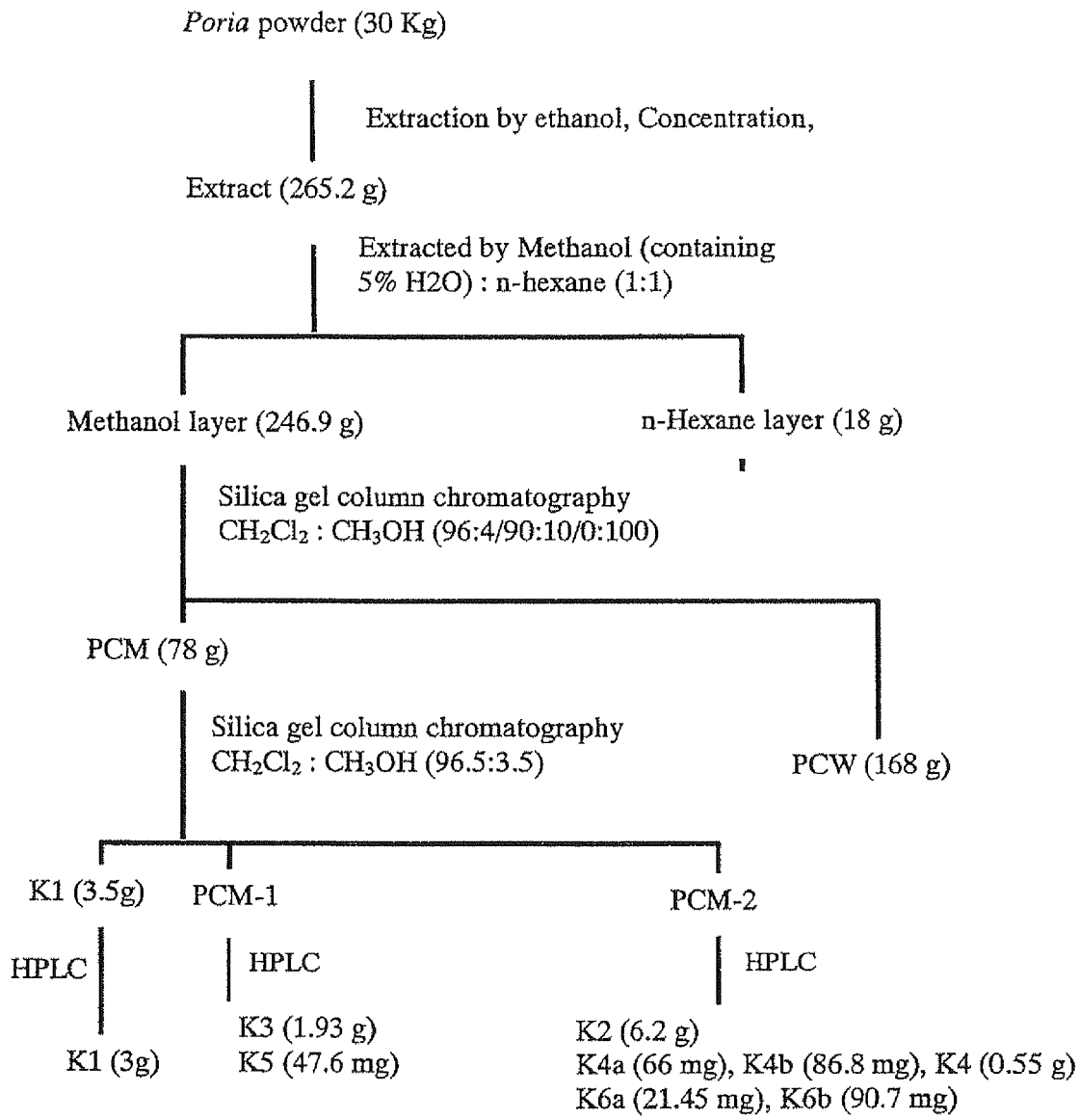
FIG. 1 shows a flow diagram of a method of the present invention for making lanostane compounds from *Poria cocos* (Schw) Wolf.

These inventors of the present invention repeated the example disclosed in the China Patent Publication No. 1008183 by using *Poria cocos* (Schw) Wolf, which was grown in China. By an acid extraction and alkaline/acidic treatments, 3 grams of a crude *Poria* extract were obtained from one kilogram of *Poria cocos* (Schw) Wolf. This is in agreement with the range of 2.5 g±0.5 g disclosed in the afore-mentioned China Patent Publication. As a result of further separation, 400 mg of purified lanostane compounds were obtained. In another words, the extract obtained according to the method disclosed in the afore-mentioned China Patent publication contains about 13% of lanostane fraction, with 87% of the extract being the secolanostane fraction and other unidentified constituents.

As a result of further experiments carried out by these inventors of the present invention, the lanostane fraction has no toxic effect on vat spleen cells and is pharmacologically effective. The secolanostane fraction has a toxic effect on rat spleen cells.

The present invention discloses a pharmaceutical composition capable of enhancing immunity of mammal, such as *Homo sapiens*. The composition contains a therapeutically effective amount of lanostane having the following chemical formula (I) as an active ingredient, and a pharmaceutically acceptable carrier or diluent for the active ingredient:

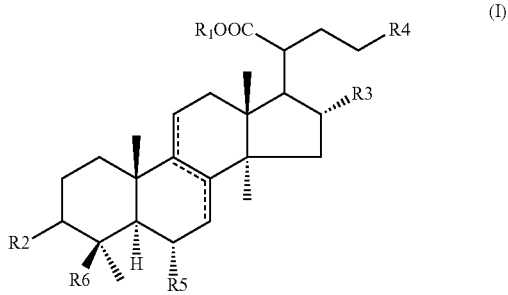

(I)

wherein $R_1$ is either H or $CH_3$; $R_2$ is $OCOCH_3$, $C=O$ or OH; $R_3$ is H or OH; $R_4$ is $-C(=CH_2)-C(CH_3)_2R_a$, wherein $R_a$ is H or OH, or $-CH=C(CH_3)-R_b$, wherein $R_b$ is $CH_3$ or $CH_2OH$; $R_5$ is H or OH; and $R_6$ is $CH_3$ or $CH_2OH$.

Preferably, the pharmaceutical composition comprises 0.1-60% of the lanostane (I) by weight of the composition and is orally administered.

The present invention also discloses a *Poria* extract capable of enhancing immunity of mammal. The extract contains 5-60%, preferably 10-20%, of the lanostane (I) by weight of the extract. The extract is substantially devoid of secolanostane.

The present invention covers a method for the preparation of the *Poria* extract. The method includes a first step in which the metabolites, the fermentation products, and the sclerotium of *Poria cocos* (Schw) Wolf are extract by a solvent, such as water, methanol, ethanol, or a mixture thereof, thereby resulting in production of a liquid extract, which is then concentrated to form a concentrated substance. The concentrated substance is introduced into a silica gel column, and is eluted with an eluent having a low polarity. As a result, an eluate is produced and collected. The eluate is concentrated to form a concentrated eluate, which has a chromatographic value (Rf)≥0.1 in accordance with a thin layer chromatography, which is developed by a mixed solvent of dichloromethane:methanol=96:4 and is detected by an ultraviolet lamp and iodine vapor.

It is suggested that the extraction is carried out by using 95% ethanol.

Preferably, the concentrated substance is further extracted with a two-phase solvent containing methanol and n-hexane in a volumetric ratio of 1:1. The methanol layer is separated and is concentrated to form a concentrate, which is used as a feed to the silica gel column.

It is recommended that the low polarity eluent is a mixed solvent containing dichloromethane and methanol in a volumetric ratio of 96.5:3.5.

Preferably, the lanostane (I) has the following structures:

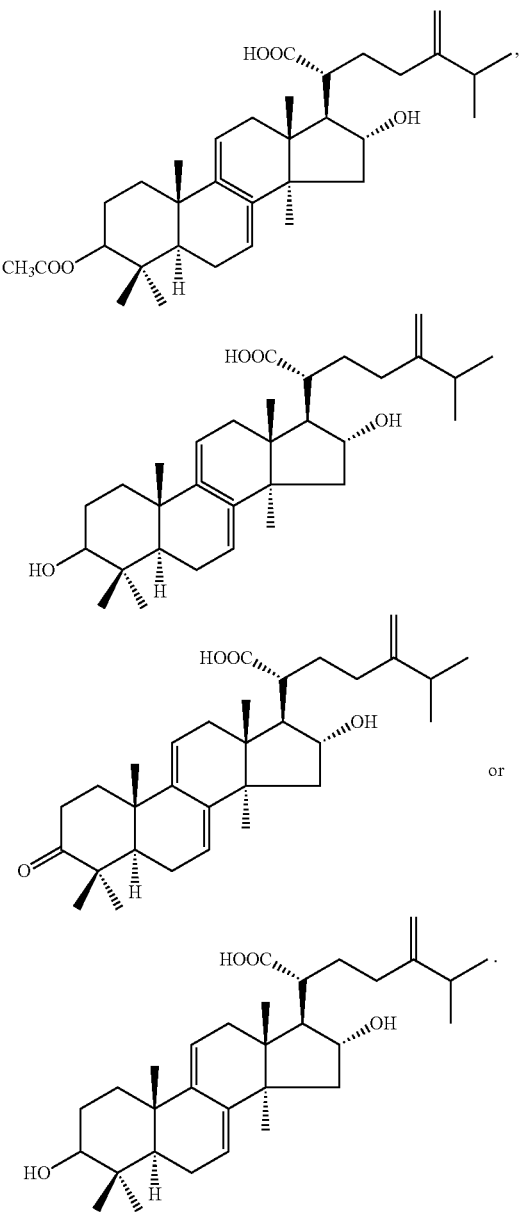

The present invention also discloses a method of enhancing immunity of an individual comprising administering to the individual a therapeutically effective amount of the lanostane (I) of the present invention.

The present invention also discloses a method of enhancing immunity of an individual comprising administering to the individual a therapeutically effective amount of the *Poria* extract of the present invention.

Example 1

As illustrated in FIG. 1, a *Poria* powder was made of 30 kilograms of the China-grown *Poria cocos* (Schw) Wolf. The *Poria* powder was extracted with 120 L 95% alcohol for 24 hours. The mixture was filtered to obtain a filtrate. The residue was extracted and filtered for another three cycles. The filtrates were combined and concentrated to bring about a dried extract in amount of 265.2 grams. The dry extract was undergone a distribution extraction with a two-phase extraction agent (n-hexane:95% methanol=1:1), and the methanol layer was removed therefrom, which is then concentrated to obtain a dry solid in an amount of 246.9 grams. A separation of the dry solid was carried out by means of a silica gel column, which was filled with silica gel 10-40 times of the weight of the dry solid. The silica gel having a diameter of 70-230 mesh was made by Merck corporation with a code of Silica Gel 60. The column was eluted by the following eluates in sequence: a mixed solvent of dichloromethane:methanol=96:4; a mixed solvent of dichloromethane:methanol=90:10, and pure methanol. The eluates were tested by the thin layer chromatography (TLC), wherein an ultraviolet lamp and iodine vapor were used for detecting, and a mixed solvent of dichloromethane:methane=96:4 was used as a developing liquid. The eluates having similar constituents in the TLC were combined.

The elution carried out with the mixed solvent of dichloromethane:methanol=96:4 resulted in a PCM portion in amount of 78 grams. The PCM shows 6 trace points in the thin layer chromatography. The resulting eluates from the elutions carried out with the eluents of dichloromethane:methanol=90:10 and pure methanol were combined to obtain a PCW portion in amount of 168 grams.

The PCM portion was further separated by means of an eluent of dichloromethane:methanol=96.5:3.5 and the silica gel column. With the thin layer chromatography, the eluates were collected as three fractions, which were respectively K1 (Rf=0.64), PCM-1 (containing trace K1, K3 (Rf=0.55), K5 (Rf=0.49)), and PCM-2 (containing K2 (Rf=0.30), K4 (Rf=0.24), K6 (Rf=0.19). The K1 fraction (3.5 g) was further subjected to a high performance liquid chromatography (HPLC) using a carbon-18 column and a mobile phase of methanol-water (90:10)). 3.0 grams of K1 component was obtained.

With the same HPLC and a mobile phase of methanol-water (87:13), the PCM-1 fraction was separated into K3, K5, and trace K1 components. The K3 component was further purified to yield K3 (1.93 g) by means of the same HPLC and a mobile phase of methanol-water (84:16). The K5 component was further purified with the same HPLC and two mobile phases of methanol-water (93:7) and (91:9) in sequence to yield K5 (47.6 mg).

With the same HPLC and a mobile phase of methanol-water (87:13), the PCM-2 fraction were separated into K6 trace component (K6a+K6b), K4 trace component (K4a+K4b), K2 component, and K4 component. By making use of the same HPLC and a mobile phase of methanol-water (84: 16), the K2 component and the K4 component were further purified to yield K2 (6.2 g) and K4 (0.55 g).

With the same HPLC and a mobile phase of $CH_3CN$-water (68:32), the K6 trace component was purified to yield K6a (21.4 mg) and K6b (90.7 mg). The K4 trace component was subjected to the same HPLC and a mobile phase of methanol-water (76:24) to yield K4a (66.0 mg) and K4b (86.8 mg).

The afore-mentioned K1-K6 compounds have analytical data as follows:

K1: mixture, EI-MS: major component, 528$[M]^+$; trace component, 526$[M]^+$

K1 (major component): $^{13}$C-NMR ($\delta$ c): 35.4 (c-1), 24.5 (c-2), 80.6 (c-3), 38.0 (c-4), 50.7 (c-5), 18.4 (c-6), 26.8 (c-7), 135.0 (c-8), 134.4 (c-9), 37.2 (c-10), 20.9 (c-11), 29.7 (c-12), 48.8 (c-13), 46.3 (c-14), 43.6 (c-15), 26.6 (c-16), 57.3 (c-17), 17.8 (c-18), 19.2 (c-19), 48.6 (c-20), 178.6 (c-21), 31.6 (c-22), 33.2 (c-23), 156.1 (c-24), 34.1 (c-25), 22.0 (c-26), 21.9 (c-27), 28.0 (c-28), 16.8 (c-29), 25.4 (c-30), 107.0 (c-31), 21.1 ($CH_3COO$—), 170.5 ($CH_3\underline{C}OO$—)

K1 (trace component): $^{13}$C-NMR ($\delta$ c): 35.6 (c-1), 24.5 (c-2), 80.6 (c-3), 37.8 (c-4), 49.7 (c-5), 23.1 (c-6), 120.6 (c-7), 142.8 (c-8), 145.8 (c-9), 37.6 (c-10), 117.0 (c-11), 36.3 (c-12), 49.4 (c-13), 45.1 (c-14), 44.4 (c-15), 76.4 (c-16), 57.6 (c-17), 17.6 (c-18), 22.8 (c-19), 48.4 (c-20), 178.5 (c-21), 31.4 (c-22), 33.2 (c-25), 156.0 (c-24), 34.1 (c-25), 22.0 (c-26), 21.9 (c-27), 28.2 (c-28), 17.1 (c-29), 26.5 (c-30), 107.0 (c-31), 21.1 ($\underline{C}H_3COO$—), 170.4 ($CH_3\underline{C}OO$—)

K2: mixture, EI-MS: major component, 486$[M]^+$; trace component, 484$[M]^+$

K2 (major component): $^{13}$C-NMR ($\delta$ c): 36.6 (c-1), 29.1 (c-2), 78.5 (c-3), 40.0 (c-4), 51.4 (c-5), 19.2 (c-6), 27.4 (c-7), 135.4 (c-8), 135.3 (c-9), 37.9 (c-10), 21.4 (c-11), 30.2 (c-12), 49.3 (c-13), 46.7 (c-14), 44.2 (c-15), 77.1 (c-16), 57.8 (c-17), 18.2 (c-18), 19.8 (c-19), 49.2 (c-20), 179.4 (c-21), 32.1 (c-22), 33.7 (c-23), 156.5 (c-24), 34.6 (c-25), 22.5 (c-26), 22.4 (c-27), 29.1 (c-28), 16.8 (c-29), 25.9 (c-30), 107.5 (c-31)

K2 (trace component): $^{13}$C-NMR ($\delta$ c): 36.7 (c-1), 29.1 (c-2), 78.5 (c-3), 40.0 (c-4), 49.8 (c-5), 24.3 (c-6), 121.2 (c-7), 143.3 (c-8), 145.2 (c-9), 38.0 (c-10), 118.1 (c-11), 37.2 (c-12), 45.5 (c-13), 49.1 (c-14), 44.8 (c-15), 76.8 (c-16), 58.0 (c-17), 18.1 (c-18), 22.9 (c-19), 48.0 (c-20), 179.4 (c-21), 31.9 (c-22), 33.7 (c-23), 156.5 (c-24), 34.6 (c-25), 22.9 (c-26), 22.4 (c-27), 29.1 (c-28), 16.8 (c-29), 26.8 (c-30), 107.5 (c-31)

K3: mp: 278-280° C.

$[\alpha]_D^{24}$+3° (c 0.6, Pyridine)

EI-MS m/z: 482$[M]^+$, $^{13}$C-NMR ($\delta$ c): 37.5 (c-1), 35.7 (c-2), 216.7 (c-3), 48.3 (c-4), 51.8 (c-5), 24.6 (c-6), 121.4 (c-7), 143.5 (c-8), 145.4 (c-9), 38.2 (c-10), 118.3 (c-11), 36.9 (c-12), 45.7 (c-13), 50.0 (c-14), 44.9 (c-15), 77.2 (c-16), 58.1 (c-17), 18.3 (c-18), 22.7 (c-19), 49.2 (c-20), 179.6 (c-21), 32.0 (c-22), 33.8 (c-23), 156.7 (c-24), 34.8 (c-25), 22.7 (c-26), 22.6 (c-27), 26.3 (c-28), 23.1 (c-29), 27.1 (c-30), 107.8 (c-31)

K4: mp:>300° C.

$[\alpha]_D^{24}$+18° (c 0.5, Pyridine)

EI-MS m/z: 484$[M]^+$, $^{13}$C-NMR ($\delta$ c): 31.4 (c-1), 27.4 (c-2), 76.0 (c-3), 38.6 (c-4), 44.5 (c-5), 24.2 (c-6), 122.0 (c-7), 143.5 (c-8), 147.4 (c-9), 38.6 (c-10), 116.9 (c-11), 37.0 (c-12), 45.9 (c-13), 50.2 (c-14), 45.1 (c-15), 77.3 (c-16), 58.2 (c-17), 18.4 (c-18), 23.7 (c-19), 49.3 (c-20), 179.8 (c-21). 32.1 (c-22), 33.9 (c-23), 156.7 (c-24), 34.9 (c-25), 22.8 (c-26), 22.6 (c-27), 29.9 (c-28), 23.9 (c-29), 27.3 (c-30), 107.9 (c-31)

K4a: mp: 284-287° C.

[α]$_D^{24}$+44° (c 0.5, Pyridine)

EI-MS m/z: 498[M]$^+$, $^{13}$C-NMR (δ c): 35.9 (c-1), 37.1 (c-2), 217.3 (c-3), 53.5 (c-4), 43.9 (c-5), 24.5 (c-6), 121.5 (c-7), 143.7 (c-8), 144.9 (c-9), 37.9 (c-10), 119.0 (c-11), 36.9 (c-12), 45.9 (c-13), 50.0 (c-14), 45.0 (c-15), 77.3 (c-16), 58.2 (c-17), 18.5 (c-18), 23.3 (c-19), 49.4 (c-20), 179.9 (c-21), 32.2 (c-22), 34.1 (c-23), 157.0 (c-24), 34.9 (c-25), 22.8 (c-26), 22.7 (c-27), 19.4 (c-28), 67.5 (c-29), 26.9 (c-30), 107.8 (c-31)

K4b: mp: 230-232° C.

[α]$_D^{24}$+38° (c 0.5, Pyridine)

EI-MS m/z: 542[M]$^+$, $^{13}$C-NMR (δ c):

36.6 (c-1), 25.0 (c-2), 82.1 (c-3), 39.4 (c-4), 56.7 (c-5), 68.9 (c-6), 129.2 (c-7), 142.1 (c-8), 145.8 (c-9), 39.2 (c-10), 117.9 (c-11), 36.9 (c-12), 45.8 (c-13), 49.9 (c-14), 44.9 (c-15), 77.3 (c-16), 58.1 (c-17), 18.4 (c-18), 24.8 (c-19), 49.3 (c-20), 179.9 (c-21), 32.1 (c-22), 33.9 (c-23). 156.7 (c-24), 34.9 (c-25), 22.8 (c-26), 22.7 (c-27), 31.9 (c-28), 18.1 (c-29), 27.1 (c-30), 107.9 (c-31), 22.0 (CH$_3$COO—), 172.0 (CH$_3$COO—)

K5: mp: 274-275° C.

[α]$_D^{24}$+10° (c 0.5, Pyridine)

EI-MS m/z: 454[M]$^+$, $^{13}$C-NMR (δ c):

36.8 (c-1), 29.6 (c-2), 79.0 (c-3), 38.6 (c-4), 50.6 (c-5), 24.3 (c-6), 122.1 (c-7), 143.6 (c-8), 147.3 (c-9), 37.2 (c-10), 117.5 (c-11), 34.1 (c-12), 45.0 (c-13), 51.3 (c-14), 30.8 (c-15), 28.1 (c-16), 48.9 (c-17), 17.4 (c-18), 23.7 (c-19), 49.9 (c-20), 179.9 (c-21), 32.4 (c-22), 27.5 (c-23), 124.3 (c-24), 132.7 (c-25), 26.6 (c-26), 18.6 (c-27), 29.2 (c-28), 17.1 (c-29), 26.7 (c-30)

K6a: mp: 248-250° C.

[α]$_D^{24}$+63° (c 0.4, Pyridine)

EI-MS m/z: 498[M]$^+$, $^{13}$C-NMR (δ c): 37.1 (c-1), 35.0 (c-2), 219.0 (c-3), 48.4 (c-4), 57.0 (c-5), 68.0 (c-6), 128.6 (c-7), 141.8 (c-8), 144.2 (c-9), 38.3 (c-10), 120.2 (c-11), 36.6 (c-12), 45.8 (c-13), 49.7 (c-14), 44.8 (c-15), 77.2 (c-16), 58.1 (c-17), 18.4 (c-18), 22.7 (c-19), 49.4 (c-20), 179.6 (c-21), 32.1 (c-22), 33.9 (c-23), 156.8 (c-24), 34.9 (c-25), 22.8 (c-26), 22.7 (c-27), 31.5 (c-28), 24.5 (c-269), 26.6 (c-30), 107.9 (c-31)

K6b: mp: 267-270° C.

[α]$_D^{24}$+68° (c 0.3, Pyridine)

EI-MS m/z: 516[M]$^+$, $^{13}$C-NMR (δ c): 34.4 (c-1), 29.4 (c-2), 74.1 (c-3), 42.6 (c-4), 87.7 (c-5), 133.1 (c-6), 134.7 (c-7), 79.6 (c-8), 145.8 (c-9), 42.1 (c-10), 120.7 (c-11), 36.8 (c-12), 49.1 (c-13), 48.7 (c-14), 42.7 (c-15), 76.8 (c-16), 57.6 (c-17), 19.0 (c-18), 29.3 (c-19), 49.1 (c-20), 179.6 (c-21), 32.2 (c-22), 33.9 (c-23), 156.8 (c-24), 34.9 (c-25), 22.9 (c-26), 22.7 (c-27), 25.1 (c-28), 20.3 (c-29), 20.8 (c-30), 107.9 (c-31)

The structures of K1 to K6 compounds are listed as follows:

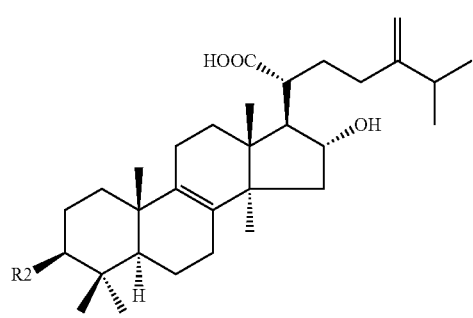

K1: R$_2$ = OCOCH$_3$, major component
K2: R$_2$ = OH, major component

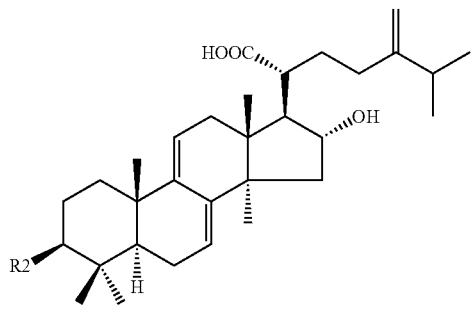

K1: R$_2$ = OCOCH$_3$, trace component
K2: R$_2$ = OH, trace component

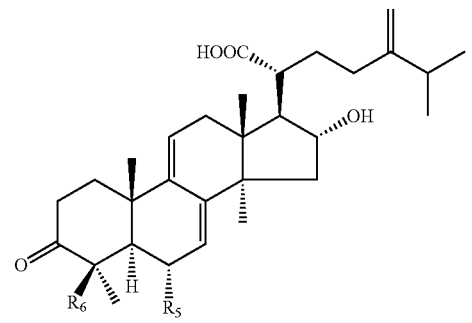

K3: R$_6$ = CH$_3$   R$_5$ = H
K4a: R$_6$ = CH$_2$OH   R$_5$ = H
K6a: R$_6$ = CH$_3$   R$_5$ = OH

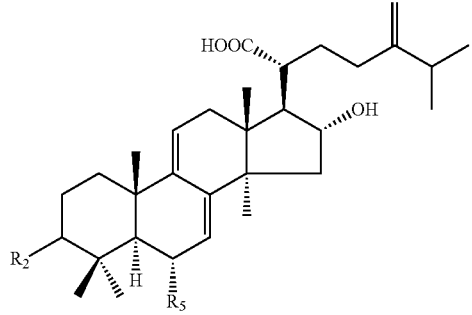

K4: R$_2$ = α-OH   R$_5$ = H
K4b: R$_2$ = β-OCOCH$_3$   R$_5$ = OH

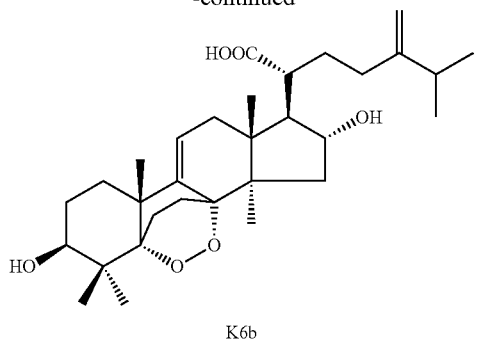

K6b

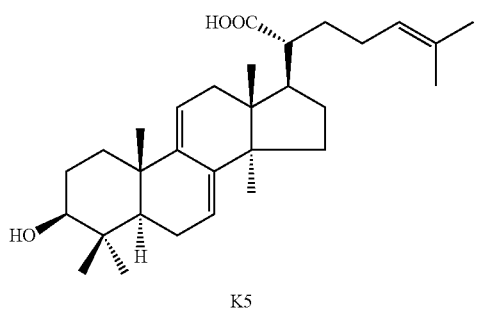

K5

Example 2

Figure 2:
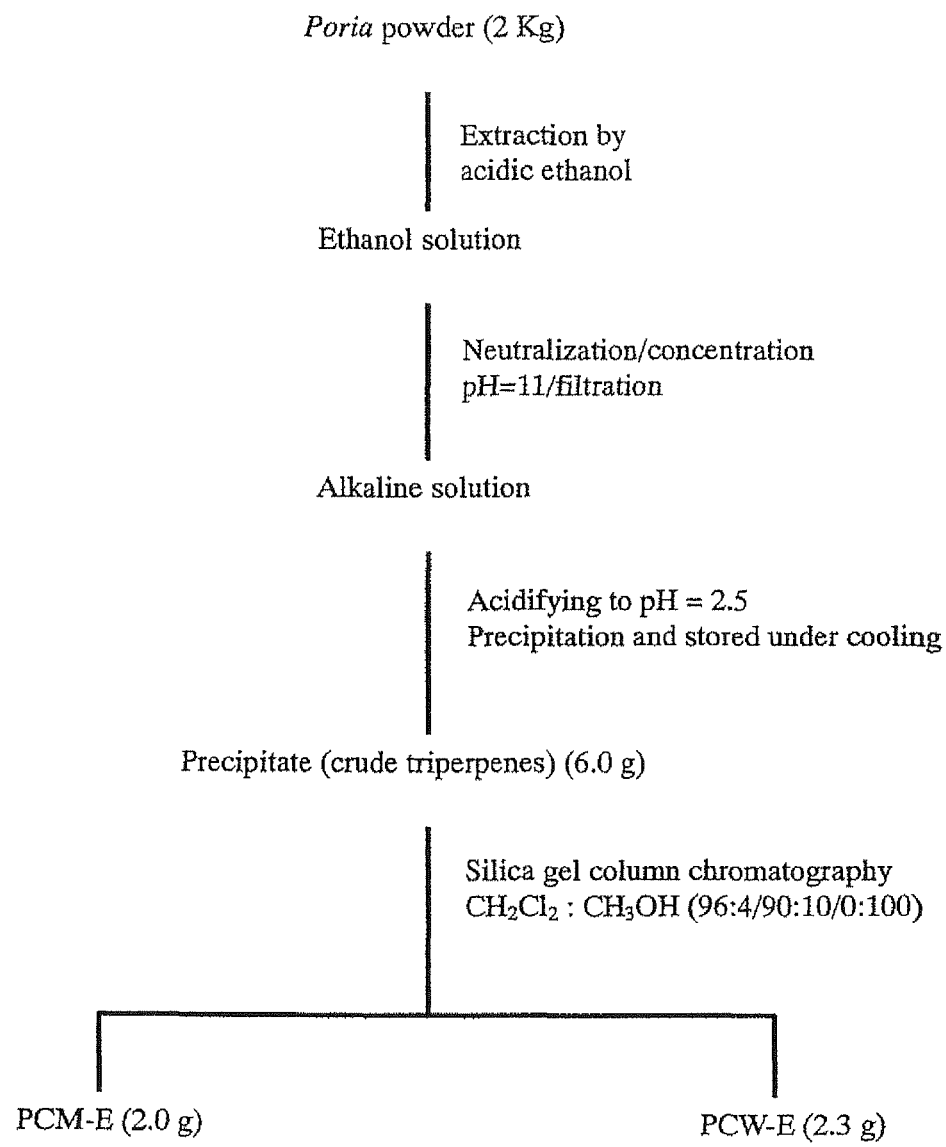
FIG. 2 shows a flow diagram of making a *Poria* extract in accordance with a method disclosed by the China Patent Publication No. 1008183, and a low polarity portion of the *Poria* extract according to the present invention.

A powder was made of two kilograms of the China-grown *Poria cocos* (Schw) Wolf. By using the method disclosed in the China Patent Publication No. 1008183, a crude extract in an amount of 6.0 g was obtained, as shown in FIG. 2. Following the procedures described in Example 1, the crude extract was subjected to a silica gel column chromatography and eluted with a mixed solvent of dichloromethane:methanol=96:4 to obtain a PCM-E portion (2.0 g), and eluted with dichloromethane:methanol=90:10 and pure methanol in sequence to obtain a PCW-E portion (2.3 g).

The PCM-E and the PCW-E prepared in Example 2 were orally administered to animals in a dose of 40 mg/kg per day for the purpose of testing the effect of these two portions on growth of spleen cells (immunity cells) of the animals. The immune system of the animals will be enhanced, if the growth of spleen cells thereof are stimulated; and will be adversely affected, if the growth of spleen cells are inhibited, i.e. the spleen cells are killed due to toxicity.

The spleen cells were cultivated in vitro for five days before they were compared for cellular growth by means of MTT assay, which was determined by an immunological research method described hereinafter. The results are listed in the Table 1. The cellular growth of the spleen of the mice was apparently promoted on the third day and the fourth day in the wake of oral administration of PCM-E. Based on the statistic view point, there is no difference in terms of cellular growth among the control group and the experimental group. However, the number of the alive spleen cells of the mice was apparently lower than that of the control group on the third day and the fourth day in the wake of oral administration of PCW-E. In another words, the cellular growth of the spleen of the experimental group is apparently weakened as compared to the control group. This means that PCW-E is cytotoxic.

The implication is that the lanostane-containing low polarity portion, PCM, has no inhibitive effect on cellular growth of the spleen. In addition, the PCM portion has a promotive effect on cellular growth of the spleen. The secolanostane-containing high polarity portion (Rf<0.1) has an inhibitive effect on cellular growth of the spleen. The *Poria* extract of the present invention is devoid of the secolanostane fraction (PCW-E). On the contrary, the *Poria* extract obtained by the prior art methods contains the PCW-E capable of inhibiting cellular growth of the spleen.

TABLE 1

| | Effects of PCM-E and PCW-E on cellular growth of spleen | | | |
|---|---|---|---|---|
| | dose | In vitro growth (day) | | |
| component | (mg/kg/day) | 3rd day | 4th day | 5th day |
| Control group | | $0.608 \pm 0.042^a$ | $0.777 \pm 0.141$ | $0.515 \pm 0.055$ |
| PCM-E | 40 | $0.890 \pm 0.195$ | $0.857 \pm 0.137$ | $0.449 \pm 0.083$ |
| PCW-E | 40 | $0.245 \pm 0.072*$ | $0.451 \pm 0.020**$ | $0.344 \pm 0.132$ |

[a] data are mean ± S.E.M. of five experiments
* is indicative of $P < 0.05$;
** is indicative of $P < 0.01$ On the basis of the above two examples and the comparative results, the following facts are established.

The potent component of the *Poria cocos* (Schw) Wolf is a lanostane-containing low polarity portion, which is capable of enhancing immunity of human body.

A silica gel thin layer chromatography and a silica gel column chromatography can be employed to separate the promotive components from the inhibitive components of *Poria cocos* (Schw) Wolf.

The *Poria* extract obtained by the method of the present invention is devoid of the inhibitive components, which are secolanostanes and high polar molecules contained in the high polarity portion, PCW-E. For this reason, the method of the present invention is superior to the prior art methods.

The animal experiments of the present invention are carried out by an oral administration of PCM-E and PCW-E to animals. In another words, the administrations of PCM-E and PCW-E of the present invention take place in vivo other than in vitro. Because in vitro study of pharmaceutical compound on spleen cells dose not reflect actual effects of the pharmaceutical compound on cellular growth of the animal spleen in light of absence of interactions between cellular metabolism and the pharmaceutical compound. It is therefore readily apparent that the present invention is reliable and meaningful.

The *Poria* extract and the purified compounds from the *Poria* extract by chromatography prepared according to the methods of the present invention were tested by various immunity response experiments listed in the following. The PCM fraction of *Poria* extract and the lanostane compounds K1, K2, K3 and K4 purified therefrom in Example 1 exhibit immunity enhancement activities in immune cells (T cells/B cells) in the following immunity response tests, and, as shown in Table 2 to Table 10, K1, K2, K3 and K4 compounds are potent at dosage low than 2.5 or 5.0 mg/kg.

Experiments

Experimental Animals

BALB/c male mice, 6-8 weeks old, were used throughout the experiment. The animals were purchased from National Laboratory Animal Center, Taipei, Taiwan. The mice were housed in the Individual Ventilation Cage System, which provided an environment of Specific Pyrogen-Free. The facilities had 12-h day/night rhythm, 24-26° C. and 30-70% humidity in air. Mice were fed autoclaved water and rodent chow, and the bedding was sterilized by autoclave also. The feedstock purchased from animal center of National Taiwan University composed of crude proteins (>23.0%), crude fat (>4.5%), crude fiber (<6.0%), ash (<8.0%), added minerals (<3.0%) and water (<12%). After transport, the mice were allowed to rest for two weeks before the experiments were started.

Animal Treatment

For the drug treatment, the animals were divided into four groups and oral administration with 1 ml of PCM, ranging from 10, 40 to 80 mg/kg/day, for four days. For the studies on the purified PCM-K1, K2, K3 and K4, the dosage of oral administration had a range from 2.5, 5, to 20 mg/kg/day, which were a quarter of the dosage used for PCM study. The control group was the mice feeding with an equal volume of saline (0.85% of NaCl). Mice were sacrificed at day five, and both the serum and spleen cells were collected. The sera were subsequently used to measure the concentration of IgG, IgM and IgA. The spleen cells were plated onto a 100 mm diameter culture plate and incubated at 37° C. for three hours. The non-adherent cells containing T-lymphocytes, B-lymphocytes and NK cells were collected and properly diluted as described in each assay.

Drug Preparation

The dry powder of PCM, PCM-K1, K-2, K-3 and K4 were suspended in sterile water, followed by sonication to break down the large particle. The suspension of fine particles was used to feed the animals.

Isolation of Spleen Lymphocytes

The mouse to be sacrificed was cervical dislocated and sterilized with 70% ethanol. The cardiac punctuation was performed first to withdraw the blood. After the haemagglutination, the blood sample was subjected to centrifugation and the serum was collect. For isolation of spleen cells, the peritoneum was opened to remove the spleen. The fresh spleen was transferred to a culture plate containing 10 ml of RPMI-1640 culture medium. The spleen was then ground over a fine mesh to release the spleen cells. The spleen cells suspending in the medium were then removed and transferred to a 50-ml conical centrifuge tube. The tube was subjected to centrifugation at 1300 rpm for 10 min. The supernatant was discarded and the pellet was re-suspended in 1 ml of cold RBC lysing buffer containing EDTA-NH$_4$Cl. The cells were incubated at room temperature for 10 min, followed by washing the cells three times with culture medium by centrifugation. The spleen cells were plated onto a 100 mm diameter culture plate and incubated at 37° C. for three hours. The non-adherent cells containing T-lymphocytes, B-lymphocytes and NK cells were collected and properly diluted as described in each assay.

MTT Assay

MTT assay is the method routinely used for estimating the viable cell number and viability of the cultured cells. The basic principle is that the only mitochondria in a viable cells contain biologically activated oxido-reductive enzymes. The enzymes interact with MTT reagents to convert the chemical into a relatively insoluble blue crystal. The crystal is then solubilized in an acidic isopropanol and the absorbence at 570 nm in each well was read using an ELISA reader (EL311, BioTek, VT). Briefly, the spleen cells suspended in a medium containing RPMI 1640 supplemented with 10% fetal bovine serum (FBS), 2 mM L-glutamine, antibiotics and 1 μg/ml concanavalin A (Con A) were cultured in the 96-well flat-bottom plate ($5 \times 10^5$ cells/100 μl/well) for 5 days. MTT assay was performed at day 3, 4 and 5. MTT tetrazolium (3-(4-5-dimethylthiazol-2-yl)-2,5-diphenyltertrazolium bromide) (5 mg/ml in phosphate-buffered saline) (Sigma Chemical, St. Louis, Mo.) was added to the spleen cells (20 μl MTT per 100 μl cells), and plates were incubated at 37° C. for 4 h. Acid-isopropanol (100 μl of 0.04 NHCL in isopropanol) was added to all wells and mixed completely to dissolve the dark blue crystals. After 20 minutes at room temperature to ensure that all crystals were dissolved, the plates were read on an EIA reader at 570 nm.

ELISA to Measure Concentration of Immunoglobulins

An ELISA was performed in our study to measure the immunoglobulin concentration. Briefly, the spleen cells ($5 \times 10^5$ cells/ml) were cultured in a medium containing RPMI 1640 supplemented with 10% fetal bovine serum (FBS), 2 mM L-glutamine, antibiotics and 5 μg/ml lipopolysaccharide (LPS; 1 μg/$10^5$ cells) for 5 days. LPS is a polyclonal activator of B lymphocyte. Culture spleen cell supernatants were collected at day 3, 4 and 5. IgA, IgG and IgM concentrations were measured using a sandwich ELISA technique.

1. IgG Assay:

A 96-well microtiter plate (Nunc-Immuno Plate, MaxiSorp, Nunc, Denmark) was precoated with 100 ng/well of capture antibodies at 4° C. overnight. The capture antibody was a rabbit anti-mouse IgG+IgA+IgM antibody (Zymed Laboratory, CA). The plate was washed with PBS-0.05%

Tween 20 solution and blocked with PBS-1% gelatin. After the blocking, the properly diluted samples ($1/10^5$ diluted) and standard IgG ranged from 0.25 µg/ml to 0.039 µg/ml were added (100 µl/well). The plate was then incubated at 37° C. for 2 h. At the end of incubation, HRP-conjugated goat anti-mouse IgG (1:2,000 diluted; anti-whole IgG molecule; Zymed Laboratory, CA) was added (100 µl/well). After 1 h of incubation at 37° C., the color was developed using a substrate solution containing 0.1 M citrate buffer, pH 4.5, 0.03% $H_2O_2$ and 0.1% of o-phenylenediamine. The absorbence at 490 nm in each well was read using an ELISA reader (EL311, BioTek, VT), and the data was analyzed using log-logit model.

2. IgM Assay:

The procedure for IgM assay was similar to that for IgG assay, except that the samples were $1/10^4$ diluted and standard IgM ranged from 1 µg/ml to 0.0156 µg/ml were added (100 µl/well). The secondary antibody for the assay was HRP-conjugated goat anti-mouse IgM (1:1,000 diluted; heavy chain-specific; Zymed Laboratory, CA).

3. IgA Assay:

The procedure for IgA assay was similar to that for IgG assay, except that the samples were $1/10^4$ diluted and standard IgA ranged from 1 µg/ml to 0.0156 µg/ml were added (100 µl/well). The secondary antibody for the assay was HRP-conjugated goat anti-mouse IgA (1:1000 diluted; Zymed Laboratory, CA).

ELISA to Measure Concentration of Cytokine

For the quantitative analysis of IFN-γ and IL-10, the spleen cells ($1 \times 10^6$ cells/ml) were cultured in a medium containing RPMI 1640 supplemented with 10% fetal bovine serum (FBS), 2 mM L-glutamine, antibiotics and 1 µg/ml concanavalin A (Con A) for 3 days. Con A is one of the polyclonal activators for T lymphocyte. Culture spleen cell supernatants were collected. The IFNγ and IL-10 concentrations were measured using a cytokine ELISA set (Cyto Set ELISA kit) purchased from R&D Systems (MN, USA).

4. IL-10 Assay:

Cyto Set ELISA was performed as follows: A 96-well microtiter plate (Nunc-Immuno Plate, MaxiSorp, Nunc, Denmark) was precoated with capture antibodies at 4° C. overnight. The capture antibody was a rat monoclonal antibody to mouse IL-10. The samples to be tested and standard IL-10 ranged from 500 pg/ml to 15.6 pg/ml were added (100 µl/well). The plate was then incubated at 37° C. for 20 min. At the end of incubation, the plate was washed five times, followed by adding the biotinylated goat anti IL-10 polyclonal antibody. The color was developed by incubating the plate with a HRP-conjugated streptoavidin (Zymed, CA, USA), followed by a substrate solution containing hydrogen peroxide and tetramethylbenzidine (TMB). The reaction continued for 30 min at room temperature, and was stopped by adding 100 µl of 2N of sulfuric acid. The absorbence at 450 nm in each well was read using an ELISA reader (EL311, BioTek, Winooski, Vt.), and the data was analyzed using log-logit model.

5. IFN-γ Assay:

Cyto Set ELISA of IFN-γ was similar to that of IL-10, except that the capture antibody was a rat monoclonal antibody to mouse IFN-γ, and secondary antibody was biotinylated goat anti IFN-γ polyclonal antibody.

Flow Cytometric Assay to Analyze T-Cell Populations

The in vivo effect of PCM on CD3 (pan-T marker), CD4 (helper T cell maker) and CD8 (Cytotoxic T cell marker) molecule expression on T-lymphocytes was evaluated by flow cytometry. CD3, CD4 and CD8 expressions were monitored using a CY-Chrome conjugated hamster anti-mouse CD3 antibody (Becton Dickinson, San Jose, Calif.), PE-conjugated hamster anti-mouse CD4 antibody (Becton Dikinson, San Jose, Calif.) and FITC-conjugated hamster anti-mouse CD8 antibody (Becton Dikinson, San Jose, Calif.), respectively. Briefly, the non-adherent spleen cells were washed three times with sterile cold PBS, followed by adjusting the cells to $1 \times 10^6$ cells/ml. Each $1 \times 10^6$ cells were mixed with 1 µl of indicated fluorescence-conjugated antibody and incubated at room temperature in the dark for 15 min. After the incubation, the cells were washed with cold PBS and were pelleted by centrifugation at 200×g for 10 min. The pellet was dispersed and mixed with 500 µl of 1.0% of paraformaldehyde. The percentage of $CD3^+$ cells in splenic lymphocytes and the percentage of $CD4^+8^-$ and $CD4^-8^+$ cells in $CD3^+$ cell population were analyzed in flow cytometry.

Assay for NK Cytotoxicity

For measuring the NK cell-mediated cytotoxicity, a LIVE/DEAD cell-mediated cytotoxicity kit (Molecular Probes, Eugene, Oreg.) was used for the assay. This two-color fluorescence assay allows direct assessment of cell-mediated cytotoxicity and yields cytotoxicity measurements that correlate well with $^{51}Cr$ release assay. The target cell using in our assay system was YAC-1 cells (ATCC, TIB-160). Briefly, the exponentially growth YAC-1 cells were harvested and washed with complete culture medium (RPMI 1640 supplemented with 10% fetal bovine serum, 2 mM L-glutamine and antibiotics). The cells were adjusted to $1 \times 10^6$ cells/ml and 20 µl of $DiOC_{18}$ (3,3'-diocatadecyloxacarbocyanine) were added for each ml of target cells. The cells were incubated at 37° C. for 20 min. The $DiOC_{18}$ reagent created a green fluorescence membrane stain on the target cells. The cells were then washed twice with PBS and suspended in complete culture medium at a concentration of $2 \times 10^5$ cells/ml. Non-adherent spleen cells (effector cells) were washed with Hank's balance salt solution for three times and suspended in complete culture medium at a concentration of $1 \times 10^7$ cells/ml. The effector cells were then two-fold diluted to $5 \times 10^6$ cells/ml and $2.5 \times 10^6$ cells/ml. To initiate the assay, the equal volume (e.g. 200 µl) of effector cells and target cells was mixed to make the final Effector:Target ratio (E:T ratio) to 50:1, 25:1 and 12.5:1, respectively. The cell mixture was incubated at 37° C. for two hours, followed by adding 50 µl of propidium iodide. The propidium iodide can penetrate into the cells with damaged plasma membranes and stain the nuclear with red fluorescence. The cells were pelleted by centrifugation at 1000×g for 30 seconds and incubated at room temperature for another 10 min. After the incubation period, the tube was tapped gently to dislodge the pellets and then vortexed to re-suspend completely. The samples were ready for analyzing in the flow cytometry. The dead target cells had coincident green-membrane and red-nuclear staining. The live target cells were green on the membrane. However, the dead effector cells had only red-nucleus staining.

Assay for Phagocytosis

The phagocytic function of peritoneal macrophages was assayed using a Vybrant Phagocytosis Assay Kit purchased from Molecular Probes Co. (Eugene, Oreg.). BALB/c mice were divided into four groups and oral administration with 1 ml of PCM-K1, ranging from 2.5 mg/kg/day to 20 mg/kg/day for four consecutive days. The control group was composed of mice injected with an equal volume of saline (0.85% of NaCl). The animals were i. p. injected with 2.5 ml of 10% proteose peptone at day two and sacrificed by cervical dislocation at day five. The peritoneal cavity was injected with 2 ml of the divalent cation-free, serum-free DMEM. The cavity was then gently massaged for 30 second, and the peritoneal fluid together with medium and peritoneal exudate cells were withdrew using a 25G syringe. The cells were washed with complete DMEM culture medium and adjusted to $1\times10^7$ cells/ml. The cells were incubated on ice for 10 min, followed by mixing $1\times10^6$ cells with $5\times10^6$ fluorescent labeled particles. The particles for phagocytosis assay were fluorescein-labeled *Escherichia coli* (K-12 strain) BioParticles (Molecular Probes, Eugene, Oreg.). The cells were divided into experimental group and control group. The experimental group was incubated for 15 min at 37° C., followed by adding 100 μl of ice cold Quenching solution (1.25 mg/ml trypan blue). The control group was incubated at 0° C., instead. The cells from both groups were washed twice with PBS and pelleted by centrifugation at 150×g for 5 min. The contaminated erythrocytes were removed by adding ACK lysing solution. The cells were re-pelleted by centrifugation at 150×g for 5 min, and the pellet was dispersed and mixed with 500 μl of 1.0% of paraformaldehyde. The amount of particles been phagocytized by the peritoneal macrophages was analyzed by flow cytometry.

Statistics

Data from the control or drug-treatment groups were tested by ANOVA. The difference between the two means was assessed using the Mann-Whitneys rank sum test. Probability values of <0.01 were considered to be significant.

Results (1) Spleen Cell Growth—Effects of PCM and PCM-K1, K-2, K3, K4

As shown in Table 2.1 and 2.2, at day 3 of in vitro culture, spleen cells isolated from mice treated with 40 mg/kg/day of PCM, 5 mg/kg/day or higher dose of PCM-K1, -K3, -K4, 10 mg/kg/day or higher dose of PCM-K2, respectively, showed an significantly augmented effect on the cell growth. The result suggested that oral administration of PCM or purified components such as PCM-K1, K2, K3 or K4 in general did affect the growth of immune cells in lymphoid organ.

TABLE 2.1

Spleen Cell growth - Effects of PCM and PCM-K1, K-2

| Components | Dosage (mg/kg/day) | Incubation time (day) | | |
|---|---|---|---|---|
| | | 3 | 4 | 5 |
| Control | | 0.359 ± 0.076[a] | 0.481 ± 0.044 | 0.414 ± 0.067 |
| PCM | 10 | 0.453 ± 0.028 | 0.398 ± 0.057 | 0.301 ± 0.059 |
| PCM | 40 | 0.551 ± 0.040* | 0.401 ± 0.031 | 0.445 ± 0.055 |
| PCM | 80 | 0.475 ± 0.083 | 0.410 ± 0.083 | 0.447 ± 0.075 |
| K1 | 2.5 | 0.497 ± 0.080 | 0.533 ± 0.070 | 0.584 ± 0.060* |
| K1 | 5 | 0.642 ± 0.078** | 0.652 ± 0.077 | 0.469 ± 0.054 |
| K1 | 10 | 0.743 ± 0.083** | 0.733 ± 0.035*** | 0.562 ± 0.025* |
| K1 | 20 | 0.634 ± 0.048** | 0.571 ± 0.091 | 0.452 ± 0.049 |
| K2 | 2.5 | 0.533 ± 0.069* | 0.460 ± 0.052 | 0.414 ± 0.054 |
| K2 | 5 | 0.489 ± 0.087 | 0.480 ± 0.072 | 0.527 ± 0.062 |
| K2 | 10 | 0.928 ± 0.078*** | 0.931 ± 0.065*** | 0.585 ± 0.041* |
| K2 | 20 | 0.655 ± 0.075** | 0.605 ± 0.072 | 0.530 ± 0.057 |

[a]Data are the absorbance at 570 nm from the result of MTT assay; Data are Mean ± S.E.M of ten similar experiments;
*indicates p < 0.05,
**indicates p < 0.01,
***indicates p < 0.001 from the control group.

TABLE 2.2

Spleen cell growth - Effects of PCM-K3 and K4

| Components | Dosage (mg/kg/day) | Incubation time (day) | | |
|---|---|---|---|---|
| | | 3 | 4 | 5 |
| Control | | 0.373 ± 0.070[a] | 0.404 ± 0.033 | 0.431 ± 0.044 |
| K3 | 5 | 1.154 ± 0.172*** | 0.841 ± 0.160* | 0.864 ± 0.194 |
| K3 | 10 | 1.020 ± 0.090*** | 0.900 ± 0.193** | 0.957 ± 0.200* |
| K3 | 20 | 1.103 ± 0.081*** | 1.068 ± 0.132*** | 0.943 ± 0.159** |
| K4 | 5 | 0.949 ± 0.101** | 0.981 ± 0.087*** | 0.862 ± 0.085** |
| K4 | 10 | 1.198 ± 0.101*** | 1.273 ± 0.147*** | 1.177 ± 0.078*** |
| K4 | 20 | 1.233 ± 0.040*** | 1.263 ± 0.041*** | 1.061 ± 0.124*** |

[a]Data are the absorbance at 570 nm from the result of MTT assay; Data are Mean ± S.E.M of six similar experiments;
*indicates p < 0.05,
**indicates p < 0.01,
***indicates p < 0.001 from the control group.

(2) Serum Levels of Immunoglobulins—Effects of PCM and PCM-K1, K-2, K3, K4

Data in Table 3.1 and 3.2 indicated that mice orally treated with 40 mg/kg/day of PCM significantly elevated the serum level of IgG. Mice treated with 5 mg/kg/day or higher dose of PCM-K1, K2 and K4, respectively, also significantly increased the serum level of IgG. By contrast, mice treated with 5 mg/kg/day or higher dose of PCM-K3 showed a significant reduction in the serum level of IgG. Mice orally treated with 40 mg/kg/day of PCM, 10 mg/kg/day of PCM-K1, 2.5 mg/kg/day of PCM-K2, 5 mg/kg/day of PCM-K3 and 5 mg/kg/day of PCM-K4, respectively, showed a significantly increase in the serum level of IgM. Oral administration of 80 mg/kg/day of PCM significantly reduced the level of IgA in mouse serum. However, mice treated with 10 mg/kg/day of PCM-K1 significantly elevated the serum level of IgA. The result from our experimental system showed no effect of PCM-K2, K3 and K4 on the serum concentrations of IgA.

TABLE 3.1

Serum level of immunoglobulins - Effect of PCM, PCM-K1, PCM-K2

| Components | Dosage (mg/kg/day) | Immunogglobulin concentrations(mg/ml) | | |
|---|---|---|---|---|
| | | IgG | IgM | IgA |
| Control | | $1.81 \pm 0.19^a$ | $0.90 \pm 0.18$ | $3.67 \pm 0.54$ |
| PCM | 10 | $2.38 \pm 0.28$ | $1.31 \pm 0.13$ | $3.40 \pm 0.25$ |
| PCM | 40 | $4.36 \pm 0.88*$ | $1.96 \pm 0.18***$ | $2.54 \pm 0.28$ |
| PCM | 80 | $4.53 \pm 0.92*$ | $2.07 \pm 0.21***$ | $2.26 \pm 0.26*$ |
| K1 | 2.5 | $1.57 \pm 0.32$ | $1.27 \pm 0.22$ | $3.51 \pm 0.33$ |
| K1 | 5 | $2.83 \pm 0.41*$ | $1.38 \pm 0.24$ | $4.03 \pm 0.47$ |
| K1 | 10 | $3.00 \pm 0.53**$ | $3.27 \pm 0.47***$ | $6.57 \pm 0.71**$ |
| K1 | 20 | $3.74 \pm 0.62**$ | $1.46 \pm 0.27$ | $3.79 \pm 0.35$ |
| K2 | 2.5 | $1.69 \pm 0.24$ | $2.82 \pm 0.41***$ | $2.85 \pm 0.36$ |
| K2 | 5 | $2.95 \pm 0.17**$ | $3.46 \pm 0.61***$ | $2.81 \pm 0.28$ |
| K2 | 10 | $3.75 \pm 0.54***$ | $2.58 \pm 0.38***$ | $4.33 \pm 0.33$ |
| K2 | 20 | $5.11 \pm 0.72***$ | $5.13 \pm 0.95***$ | $5.02 \pm 0.65$ |

$^a$Data are Mean ± S.E.M of ten similar experiments;
*indicates p < 0.05,
**indicates p < 0.01,
***indicates p < 0.001 from the control group.

TABLE 3.2

Serum level of immunoglobulins - Effect of PCM-K3, PCM-K4

| Components | Dosage (mg/kg/day) | Immunoglobulin concentrations (mg/ml) | | |
|---|---|---|---|---|
| | | IV | IgM | IgA |
| Control | | $1.80 \pm 0.11$ | $1.11 \pm 0.13$ | $3.15 \pm 0.48$ |
| K3 | 5 | $1.32 \pm 0.09**$ | $1.63 \pm 0.11**$ | $3.65 \pm 0.26$ |
| K3 | 10 | $1.28 \pm 0.13**$ | $1.53 \pm 0.14*$ | $3.81 \pm 0.46$ |
| K3 | 20 | $1.14 \pm 0.11**$ | $1.53 \pm 0.13*$ | $3.55 \pm 0.37$ |
| K4 | 5 | $3.75 \pm 0.18***$ | $2.65 \pm 0.21**$ | $3.33 \pm 0.13$ |
| K4 | 10 | $4.33 \pm 0.29***$ | $2.86 \pm 0.16**$ | $3.39 \pm 0.25$ |
| K4 | 20 | $4.18 \pm 0.25***$ | $2.36 \pm 0.16**$ | $3.54 \pm 0.12$ |

$^a$Data are Mean ± S.E.M of six similar experiments;
*indicates p < 0.05,
**indicates p < 0.01,
***indicates p < 0.001 from the control group.

(3) Immunoglobulin Secreted by Splenic B Lymphocyte—Effects of PCM and PCM-K1, K-2, K3, K4(I, 3.1 IgG Secretion by Spleen Cells In Vitro As shown in Table 4.1 and 4.2, after three days of in vitro culture, spleen cells isolated from mice treated with 40 mg/kg/day of PCM, 5 mg/kg/day or higher dose of PCM-K1 and 10 mg/kg/day or higher dose of PCM-K2, respectively, showed a significant increase in IgG secretion. On the contrary, PCM-K3 significantly suppressed the IgG secretion. Spleen cells isolated from the mice treated with 5 mg/kg/day or higher dose of PCM-K4 showed an significantly augmented effect on IgG secretion at day 5. Result from this experiment suggested that oral administration of PCM or purified components such as PCM-K1, K2 or K4 in general did increase the potential of spleen B cells to secret IgG.

TABLE 4.1

IgG secretion by Spleen Cell - Effects of PCM and PCM-K1, K-2

| Components | Dosage (mg/kg/day) | Incubation time (day) | | |
|---|---|---|---|---|
| | | 3 | 4 | 5 |
| Control | | 7.40 ± 1.07 [a] | 10.00 ± 1.42 | 11.21 ± 1.31 |
| PCM | 10 | 4.24 ± 0.69 | 6.00 ± 0.97* | 6.46 ± 0.94* |
| PCM | 40 | 16.37 ± 3.11* | 17.42 ± 3.41 | 13.67 ± 3.73 |
| PCM | 80 | 10.84 ± 3.42 | 8.67 ± 3.33 | 9.20 ± 3.18 |
| K1 | 2.5 | 19.65 ± 5.73 | 19.88 ± 5.26 | 13.34 ± 3.66 |
| K1 | 5 | 41.53 ± 8.68*** | 32.94 ± 8.84*** | 33.27 ± 6.14** |
| K1 | 10 | 38.4 ± 11.09*** | 30.01 ± 7.40*** | 34.4 ± 8.27*** |
| K1 | 20 | 59.5 ± 13.04*** | 65.55 ± 17.30*** | 70.58 ± 20.47*** |
| K2 | 2.5 | 8.32 ± 2.53 | 15.32 ± 3.67 | 9.02 ± 2.34 |
| K2 | 5 | 5.97 ± 2.70* | 10.48 ± 3.77 | 13.34 ± 3.83 |
| K2 | 10 | 12.95 ± 2.17* | 11.94 ± 2.24 | 17.97 ± 2.07** |
| K2 | 20 | 25.93 ± 10.15* | 27.41 ± 10.98* | 22.82 ± 5.96* |

[a] Data are Mean ± S.E.M of ten similar experiments;
*indicates $p < 0.05$,
**indicates $p < 0.01$,
***indicates $p < 0.001$ from the control group.

TABLE 4.2

IgG secretion by Spleen Cell - Effects of PCM-K3, K-4

| Components | Dosage (mg/kg/day) | Incubation time (day) | | |
|---|---|---|---|---|
| | | 3 | 4 | 5 |
| Control | | 7.17 ± 0.89 | 12.04 ± 0.46 | 9.55 ± 0.77 |
| K3 | 5 | 3.85 ± 0.73** | 3.43 ± 0.40** | 4.46 ± 0.95** |
| K3 | 10 | 3.18 ± 0.55** | 3.16 ± 0.62** | 3.48 ± 0.43** |
| K3 | 20 | 6.12 ± 0.70 | 7.10 ± 1.39* | 8.56 ± 1.34 |
| K4 | 5 | 12.55 ± 3.08 | 12.99 ± 0.86 | 18.29 ± 0.92** |
| K4 | 10 | 6.54 ± 1.43 | 15.15 ± 5.16 | 22.59 ± 5.35* |
| K4 | 20 | 21.23 ± 3.19** | 19.11 ± 4.23 | 22.56 ± 3.84* |

[a] Data are Mean ± S.E.M of six similar experiments;
*indicates $p < 0.05$,
**indicates $p < 0.01$,
***indicates $p < 0.001$ from the control group.

3.2 IgM Secretion by Spleen Cells In Vitro

Data on Table 5.1 and 5.2 indicated that, after three days of in vitro culture, spleen cells isolated from mice treated with 40 mg/kg/day of PCM, 10 mg/kg/day or higher dose of PCM-K1, 2.5 mg/kg/day or higher dose of PCM-K2, 10 mg/kg/day of PCM-K3 and 5 mg/kg/day or higher dose of PCM-K4, respectively, showed a significant increase in IgM secretion. Result from this experiment suggested that oral administration of PCM or purified components such as PCM-K1, K2, K3 or K4 did increase the potential of spleen B cells to secret IgM.

TABLE 5.1

IgM secretion by Spleen Cell - Effects of PCM and PCM-K1, K-2

| Components | Dosage (mg/kg/day) | Incubation time (day) | | |
|---|---|---|---|---|
| | | 3 | 4 | 5 |
| Control | | 138.27 ± 42.55 [a] | 171.10 ± 39.90 | 184.29 ± 30.97 |
| PCM | 10 | 184.37 ± 36.35 | 251.78 ± 37.64 | 273.91 ± 33.30 |
| PCM | 40 | 375.07 ± 13.6*** | 352.16 ± 7.6*** | 323.52 ± 13.7*** |
| PCM | 80 | 328.96 ± 24.46*** | 322.79 ± 23.76* | 296.89 ± 12.42** |
| K1 | 2.5 | 181.30 ± 34.26 | 201.03 ± 33.98 | 190.20 ± 38.67 |
| K1 | 5 | 223.32 ± 51.46 | 233.67 ± 31.32 | 249.35 ± 38.32 |
| K1 | 10 | 356.52 ± 28.8*** | 362.17 ± 31.1** | 527.33 ± 41.0*** |
| K1 | 20 | 267.18 ± 58.97 | 280.79 ± 32.08* | 320.44 ± 41.39* |
| K2 | 2.5 | 378.0 ± 55.5*** | 479.8 ± 60.9*** | 254.4 ± 30.8 |
| K2 | 5 | 457.81 ± 87.3** | 507.62 ± 91.9** | 334.75 ± 48.7* |
| K2 | 10 | 540.23 ± 68.8*** | 512.47 ± 4.2*** | 550.54 ± 50.1*** |
| K2 | 20 | 837.1 ± 114.5*** | 695.2 ± 144.7** | 591.5 ± 108.4*** |

[a] Data are Mean ± S.E.M of ten similar experiments;
*indicates $p < 0.05$,
**indicates $p < 0.01$,
***indicates $p < 0.001$ from the control group.

TABLE 5.2

IgM secretion by Spleen Cell - Effects of PCM-K3, K-4

| Components | Dosage (mg/kg/day) | Incubation time (day) | | |
|---|---|---|---|---|
| | | 3 | 4 | 5 |
| Control | | 121.91 ± 34.35 | 200.75 ± 32.77 | 219.30 ± 18.60 |
| K3 | 5 | 222.42 ± 42.83 | 214.45 ± 28.51 | 277.52 ± 101.63 |
| K3 | 10 | 287.66 ± 44.44* | 294.30 ± 30.68* | 309.51 ± 30.88* |
| K3 | 20 | 372.14 ± 69.48* | 519.53 ± 52.63*** | 606.44 ± 88.10** |
| K4 | 5 | 463.65 ± 76.41*** | 688.17 ± 85.78*** | 649.89 ± 70.09*** |
| K4 | 10 | 514.45 ± 70.30*** | 733.58 ± 95.70*** | 807.32 ± 104.21*** |
| K4 | 20 | 747.6 ± 128.42*** | 746.50 ± 157.76*** | 857.49 ± 92.19*** |

[a] Data are Mean ± S.E.M of six similar experiments;
*indicates $p < 0.05$,
**indicates $p < 0.01$,
***indicates $p < 0.001$ from the control group.

3.3 IgA Secretion by Spleen Cells In Vitro

Results showing on Table 6.1 and 6.2 indicated that, after three days of in vitro culture, spleen cells isolated from mice treated with 40 mg/kg/day of PCM, 5 mg/kg/day had a significant reduction in IgA secretion in comparison with control group. However, mice treated with the purified components showed a rather different result. Oral administration of 10 mg/kg/day or higher dose of PCM-K1 resulted in an increase in IgA secretion by spleen cells in vitro at day 3 and day 5. Spleen cells isolated from the mice treated with 10 mg/kg/day or higher dose of PCM-K2 and 5 mg/kg/day or higher dose of PCM-K4, respectively, showed a significant increase in IgA secretion. On the contrary, PCM-K3 significantly suppressed the IgA secretion. Result from this experiment suggested that oral administration of PCM had an opposite effect between serum level of IgA and the secretion of IgA by spleen cells. However, the purified components such as PCM-K1, K2 or K4 in general did increase the potential of spleen B cells to secret IgA.

TABLE 6.1

IgA secretion by Spleen Cell - Effects of PCM and PCM-K1, K-2

| Components | Dosage (mg/kg/day) | Incubation time (day) | | |
|---|---|---|---|---|
| | | 3 | 4 | 5 |
| Control | | 130.48 ± 30.76 [a] | 144.72 ± 31.06 | 128.56 ± 35.52 |
| PCM | 10 | 50.67 ± 13.28** | 66.09 ± 8.68* | 74.73 ± 15.17 |
| PCM | 40 | 84.31 ± 8.09 | 94.72 ± 10.64 | 125.41 ± 8.51 |
| PCM | 80 | 36.03 ± 4.10** | 46.16 ± 5.09** | 56.05 ± 7.71* |
| K1 | 2.5 | 118.64 ± 19.79 | 94.65 ± 53.54 | 108.37 ± 16.01 |
| K1 | 5 | 148.60 ± 24.55 | 127.93 ± 66.0 | 148.81 ± 22.97 |
| K1 | 10 | 32.11 ± 48.1*** | 378.5 ± 196.2*** | 422.74 ± 6.67** |
| K1 | 20 | 145.93 ± 26.52 | 144.08 ± 84.36 | 179.0 ± 18.86 |
| K2 | 2.5 | 133.90 ± 33.39 | 181.00 ± 47.98 | 277.13 ± 101.1 |
| K2 | 5 | 155.67 ± 18.66 | 142.89 ± 26.86 | 94.91 ± 12.07 |
| K2 | 10 | 239.64 ± 43.1* | 258.20 ± 46.4* | 260.00 ± 0.93* |
| K2 | 20 | 273.20 ± 54.87* | 211.48 ± 57.82 | 324.7 ± 153.4** |

[a] Data are Mean ± S.E.M of ten similar experiments;
*indicates $p < 0.05$,
**indicates $p < 0.01$,
***indicates $p < 0.001$ from the control group.

TABLE 6.2

IgA secretion by Spleen Cell - Effects of PCM-K3, K-4

| Components | Dosage (mg/kg/day) | Incubation time (day) | | |
|---|---|---|---|---|
| | | 3 | 4 | 5 |
| Control | | 58.21 ± 12.63 | 66.92 ± 17.16 | 73.41 ± 14.64 |
| K3 | 5 | 32.83 ± 7.00 | 27.37 ± 5.83* | 21.96 ± 4.17** |
| K3 | 10 | 26.57 ± 3.68* | 28.97 ± 5.95* | 18.87 ± 2.66** |
| K3 | 20 | 43.08 ± 4.05 | 43.45 ± 5.92 | 30.50 ± 3.60* |
| K4 | 5 | 55.56 ± 4.71 | 79.51 ± 3.74 | 106.69 ± 7.29* |
| K4 | 10 | 66.43 ± 5.26 | 95.39 ± 10.08 | 121.97 ± 12.69* |
| K4 | 20 | 119.59 ± 15.08** | 101.53 ± 25.08 | 133.16 ± 20.09* |

[a] Data are Mean ± S.E.M of six similar experiments;
*indicates $p < 0.05$,
**indicates $p < 0.01$,
***indicates $p < 0.001$ from the control group.

(4) $T_H1$-Type and $T_H2$-Type Cytokines Secreted by Splenic T Lymphocytes—Effects of PCM and PCM-K1, K-2, K3, K4

$T_H1$-type cytokines, such as interleukin-2 (IL-2), interferon-γ (IFN-γ) induces the cellular immune response. Whereas, $T_H2$-type cytokines, such as interleukin-4 (IL-4), interleukin-5 (IL-5), interleukin-6 (IL-6), stimulates the B lymphocyte-mediated humoral immune response. To demonstrate the role of PCM and its purified components in immunological regulation, the potential of $T_H1$-type and $T_H2$-type cytokines secreted by splenic T lymphocytes was studied. Spleen cells isolated from the mice treated with PCM and its purified components, such as PCM-K1, -K2, -K3 and K4, were cultured for five days in the presence of ConA. The amount of interferon-γ (IFNγ; TH1-type cytokine) and interleukin-10 (IL-10; TH2-type cytokine) secreted by the spleen T lymphocytes was measured (Table 7.1 & Table 7.2). After the mice were fed with 10 mg and 80 mg/kg/day of PCM, 2.5 mg/kg/day or higher dose of PCM-K1, 2.5 mg/kg/day or higher dose of PCM-K2, 5 mg and 10 mg/kg/day of PCM-K3, and 20 mg/kg/day of PCM-K4, respectively, the IFNγ secretion by ConA-stimulated splenic T cells was significantly augmented. However, the spleen cells isolated from the mice treated with 40 mg/kg/day or higher dose had no effect on IL-10 secretion. Mice treated with 2.5 mg/kg/day or higher dose of PCM-K1, 2.5 mg and 20 mg/kg/day of PCM-K2, respectively, significantly increased the secretion of IL-10 by spleen cells. Taken together, PCM was able to positively regulate $T_H1$-type cytokine at relatively low dose but it failed to regulate Th2-type cytokine secretion. However, the purified components, such as PCM-K1 and -K2, were able to augment both $T_H1$-type and $T_H2$-type cytokines secreted.

TABLE 7.1

IFN-γ and IL-10 secretion by Spleen Cell - Effects of PCM and PCM-K1, K-2

| Components | Dosage (mg/kg/day) | Cytokines (pg/ml) | |
|---|---|---|---|
| | | IFN-γ | IL-10 |
| Control | | 254.14 ± 55.68 [a] | 103.91 ± 20.36 |
| PCM | 10 | 465.11 ± 26.6** | 115.90 ± 17.29 |
| PCM | 40 | 264.79 ± 48.36 | 77.31 ± 9.31 |
| PCM | 80 | 433.44 ± 31.10** | 181.97 ± 33.26 |
| K1 | 2.5 | 428.7 ± 38.9* | 170.28 ± 13.0* |
| K1 | 5 | 673.33 ± 96.73** | 178.76 ± 24.56* |
| K1 | 10 | 682.28 ± 73.78** | 176.17 ± 45.24 |
| K1 | 20 | 783.97 ± 76.1*** | 334.7 ± 45.8*** |
| K2 | 2.5 | 414.80 ± 31.3* | 135.71 ± 19.89 |
| K2 | 5 | 432.70 ± 50.22* | 226.48 ± 55.67* |
| K2 | 10 | 348.45 ± 72.56* | 135.62 ± 48.15 |
| K2 | 20 | 457.48 ± 57.60** | 195.27 ± 40.0* |

[a] Data are Mean ± S.E.M of ten similar experiments;
*indicates p < 0.05,
**indicates p < 0,01,
***indicates p < 0.001 from the control group.

TABLE 7.1

IFN-γ and IL-10 secretion by Spleen Cell - Effects of PCM-K3, K-4

| Components | Dosage (mg/kg/day) | Cytokines (pg/ml) | |
|---|---|---|---|
| | | IFN-γ | IL-10 |
| Control | | 124.25 ± 28.15 [a] | 107.80 ± 20.79 |
| K3 | 5 | 917.07 ± 130.41* | 262.09 ± 108.41 |
| K3 | 10 | 449.74 ± 100.67* | 86.48 ± 33.26 |
| K3 | 20 | 176.20 ± 45.96 | 98.74 ± 27.05 |
| K4 | 5 | 240.45 ± 107.83 | 128.91 ± 45.46 |
| K4 | 10 | 252.26 ± 103.76 | 197.39 ± 68.73 |
| K4 | 20 | 292.00 ± 77.77* | 155.91 ± 26.16 |

[a] Data are Mean ± S.E.M of six similar experiments;
*indicates p < 0.05,
**indicates p < 0.01,
***indicates p < 0.001 from the control group.

(5) Spenic T Lymphocyte Population—Effects of PCM $CD4^+8^-$ T-cells are predominantly helper T-cells ($T_H$), and $CD4^-8^+$ T-cells are mainly cytotoxic T-lymphocytes (CTL). To demonstrate the role of PCM and its purified components in modulation of T lymphocyte sub-population, the percentages of $CD4^+$ and $CD8^+$ cells in non-adherent spleen cell were analyzed by FASC. Mice were fed with PCM ranged from 10 mg/kg/day to 80 mg/kg/day for four consecutive days. The animals were sacrificed at day 5 and non-adherent spleen cells isolated. The PCM-treated mice showed no significant effect on the percentage of $CD4^+8^-$ cells (Table 8). although there was a tendency of increase as the dose was raised to 80 mg/kg/day. However, the PCM-treated mice showed a significantly increase in $CD4^-8^+$ cells subset (Table 8). In other words, the cytotoxic T lymphocyte population was increased after the mice were fed with PCM. The differentiation of CTL is mainly induced by Th1-type cytokines. Therefore, this finding correlated well with the augmented effect of PCM on IFN-γ secretion. Since the $CD4^+8^-$ cells subset also showed a tendency of increase, we did not observed an increase in CD4/CD8 ratio in spleen lymphocyte population.

TABLE 8

Regulation of T-lymphocyte subpopulation - effect of PCM

| Components | Dosage (mg/kg/day) | Fluorescent-positive cells (%) | | |
|---|---|---|---|---|
| | | CD4 | CD8 | CD4/CD8 |
| Control | | 23.40 ± 2.31 [a] | 12.50 ± 0.82 | 1.87 |
| PCM | 10 | 28.67 ± 2.54 | 15.31 ± 0.72* | 1.87 |
| PCM | 40 | 27.72 ± 0.66 | 16.67 ± 1.08** | 1.66 |
| PCM | 80 | 29.95 ± 2.75 | 16.76 ± 1.29** | 1.79 |

[a] Data are Mean ± S.E.M of five similar experiments;
*indicates p < 0.05,
**indicates p < 0.01 from the control group.

(6) Cytotoxic Activity of NK Cell—Effects of PCM

NK cells play a pivotal role in innate immunity. NK cells non-specifically kill the tumor cells (transformed cells) and viral infected cells. Non-adherent spleen cells isolated from PCM-treated mice were immediately used for NK-mediated cytotoxicity assay. Result indicated that PCM induced an increase in NK-mediated cytotoxicity at 10 mg/kg/day (Table 9). When the dose of PCM was increased, the NK cell activity returned to the basal level. The activation of NK cells is mainly stimulated by Th1-type cytokines. Therefore, this finding correlated well with the augmented effect of PCM on IFN-γ secretion.

TABLE 9

Nature killer cell activity-Effect of PCM

| Components | Dosage (mg/kg/day) | Target : Effector | | |
|---|---|---|---|---|
| | | 1 : 12.5 | 1 : 25 | 1 : 50 |
| Control | | 16.57 ± 0.61 [a] | 17.04 ± 1.06 | 16.57 ± 0.61 |
| PCM | 10 | 14.24 ± 2.18 | 20.78 ± 1.25 | 23.12 ± 2.86* |
| PCM | 40 | 18.62 ± 2.62 | 18.20 ± 2.02 | 20.99 ± 3.59 |
| PCM | 80 | 15.54 ± 3.49 | 18.27 ± 2.05 | 16.35 ± 0.90 |

[a] Data are percentage of target cells (YAC-1 cells) which are killed by the NK cells in spleen cell population. The dead cells are propedium iodide-positive; Data are Mean ± S.E.M of five similar experiments;
*indicates p < 0.05 from the control group.

(7) Phagocytic Activity of Macrophages—Effects of PCM

Phagocytic cells are involved in the first line defense against invading pathogens. The predominant phagocytic cells in innate immunity are neutrophils and macrophages. In this study, the peritoneal exudated macrophages were fed with the fluorescent-labeled *E. coli*, and assayed for the phagocytic activity of elicited macrophages. An average 20.88% of macrophages isolated from control group showed phagocytic activity. However, the percentage of cells showing phagocytic activity was 27.49% and 38.22% after the mice were fed with PCM at 40 mg/kg/day and 80 mg/kg/day, respectively, suggesting that PCM significantly enhance the phagocytic activity of peritoneal macrophages.

TABLE 10

Phagocytosis of peritoneal exudates macrophages-Effect of PCM

| Components | Dosage (mg/kg/day) | Phagocytosis |
| --- | --- | --- |
| Control |  | 20.88 ± 3.90 [a] |
| PCM | 10 | 17.08 ± 1.82 |
| PCM | 40 | 27.49 ± 3.99* |
| PCM | 80 | 38.22 ± 2.20** |

[a] Data are percentage of macrophages that ingests fluorescent-labeled *E. coli*; Data are Mean ± S.E.M of ten similar experiments;
*indicates p < 0.05,
**indicates p < 0.01 from the control group.

What is claimed is:

1. A method of enhancing immunity of an individual comprising administering to the individual a composition that contains a lanostane, the composition being substantially devoid of secolanostane, wherein the lanostane is

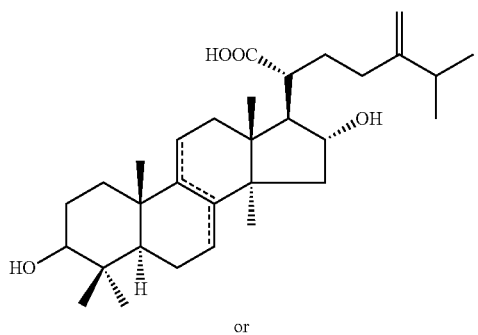

or

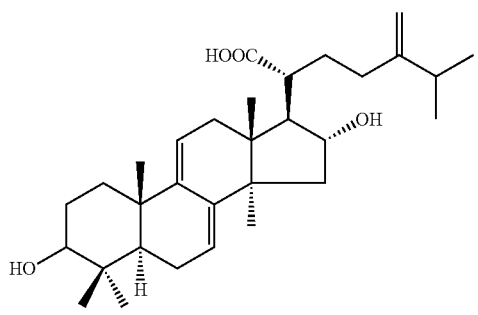

and wherein the amount of the composition administered to the individual is effective for increasing in the individual, as compared with a control, growth of spleen cells or the serum level of an immunoglobulin selected from the group consisting of IgG, IgM, and IgA.

2. The method of claim 1, wherein the composition is a *Poria* extract, the *Poria* extract has a chromatographic value Rf, not less than 0.1 in accordance with a thin layer chromatography, which is developed by a mixed solvent of dichloromethane:methanol=96:4 and is detected by an ultraviolet lamp and iodine vapor.

3. The method of claim 2, wherein the *Poria* extract is prepared by a method comprising the following steps:

a) extracting metabolites, fermentation products or sclerotium of *Poria cocos* (Schw) Wolf by water, methanol, ethanol, or a mixed solvent thereof;

b) concentrating the resulting liquid extract from step a);

c) introducing the resulting concentrated substance from step b) into a silica gel column;

d) eluting the silica gel column with an eluent having a low polarity, and collecting the resulting eluate;

e) concentrating the eluate to form a concentrated eluate, wherein said eluent having a low polarity is so selected such that the concentrated eluate has a chromatographic value, Rf, not less than 0.1 in accordance with a thin layer chromatography, which is developed by a mixed solvent of dichloromethane:methanol=96:4 and is detected by an ultraviolet lamp and iodine vapor.

4. The method of claim 3, wherein the extraction in step a) is carried out by using 95% ethanol.

5. The method of claim 3, wherein the concentrated substance resulted from step b) is further extracted with a two-phase solvent containing methanol and n-hexane in a volumetric ratio of 1:1, a methanol layer is separated from the two-phase solvent extraction mixture, and the methanol layer is concentrated to form a concentrate, which is used as a feed to the silica gel column in step c).

6. The method of claim 3, wherein the low polarity eluent is a mixed solvent containing dichloromethane and methanol in a volumetric ratio of 96.5:3.5.

7. The method of claim 2, wherein the *Poria* extract contains 5-60% of the lanostane.

8. The method of claim 1, wherein the composition contains an isolated lanostane selected from the group consisting of

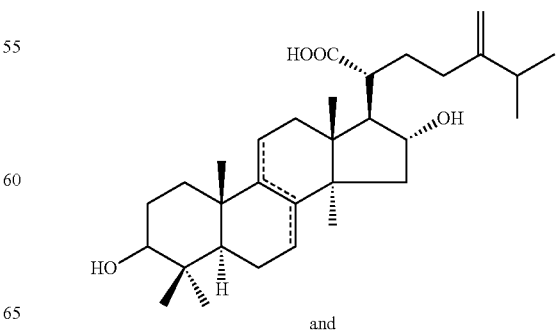

and

9. The method of claim 8, wherein the isolated lanostane is

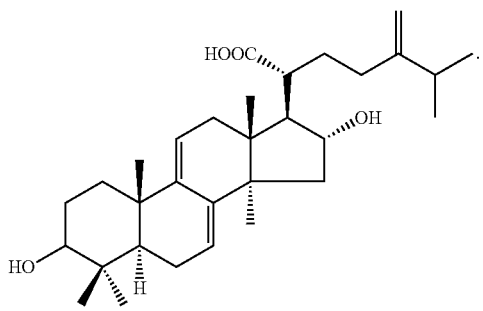

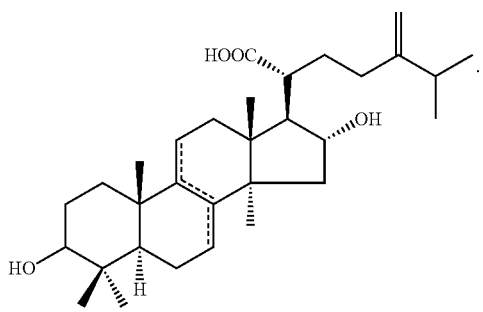

10. The method of claim 8, wherein the isolated lanostane is

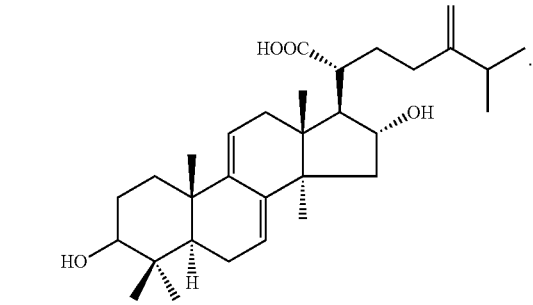

11. The method of claim 1, wherein the amount administered is effective for increasing both growth of spleen cells and the serum level of an immunoglobulin.

12. The method of claim 1, wherein 2.5 to 20 mg/kg/day of the lanostane is administered.

13. The method of claim 12, wherein 5 to 20 mg/kg/day of the lanostane is administered.

14. The method of claim 12, wherein 2.5, 5, 10, or 20 mg/kg/day of the lanostane is administered.

15. The method of claim 2, wherein 10-80 mg/kg/day of the composition is administered.

16. The method of claim 15, wherein 10, 40, or 80 mg/kg/day of the composition is administered.

* * * * *